United States Patent [19]

Greenwald et al.

[11] Patent Number: 5,349,001
[45] Date of Patent: Sep. 20, 1994

[54] CYCLIC IMIDE THIONE ACTIVATED POLYALKYLENE OXIDES

[75] Inventors: Richard B. Greenwald, Somerset; Anthony J. Martinez, Hamilton Square, both of N.J.

[73] Assignee: Enzon, Inc., Piscataway, N.J.

[21] Appl. No.: 6,247

[22] Filed: Jan. 19, 1993

[51] Int. Cl.$^5$ .............. C08G 65/32; C08L 67/00; C08L 71/02; C08L 77/00
[52] U.S. Cl. .............. 525/408; 548/157; 548/188; 548/462; 548/514
[58] Field of Search ............ 525/408; 548/157, 188, 548/462, 514

[56] References Cited

U.S. PATENT DOCUMENTS

| | | | |
|---|---|---|---|
| 4,492,657 | 1/1985 | Heiss | 260/453.7 |
| 4,495,355 | 1/1985 | Fujita et al. | 548/188 |
| 5,122,614 | 6/1992 | Zalipsky | 548/435 |

FOREIGN PATENT DOCUMENTS 0236987 9/1987 European Pat. Off. .
0539167 4/1993 European Pat. Off. .

OTHER PUBLICATIONS

Structure Display for Chemical Abstract 112(14):129084r.
Fujita, *Pure & Appl. Chem.*, 53(6), 1141-54 (1981).
Eguchi et al., *Eur. J. Biocham.*, 155, 415-21 (1986).

*Primary Examiner*—Frederick Krass
*Attorney, Agent, or Firm*—Michael N. Mercanti

[57] ABSTRACT

Water-soluble cyclic imide thione activated polyalkylene oxides having improved hydrolytic stability are disclosed. Methods of forming and conjugating the activated polyalkylene oxides with biologically active nucleophiles are also disclosed.

10 Claims, No Drawings

CYCLIC IMIDE THIONE ACTIVATED POLYALKYLENE OXIDES

BACKGROUND OF THE INVENTION

The present invention relates to cyclic imide thione activated polyalkylene oxides (PAO's) having improved hydrolytic stability, and to water-soluble polyalkylene oxide conjugates prepared therefrom. The present invention particularly relates to thiazolidinethione activated polyalkylene oxides.

The conjugation of water-soluble polyalkylene oxides with useful molecules such as proteins and polypeptides is well known. The coupling of peptides and polypeptides to polyethylene glycol (PEG) and similar water-soluble polyalkylene oxides is disclosed by U.S. Pat. No. 4,179,337 to Davis et al.

Davis et al. discloses that physiologically active polypeptides modified with PEG exhibit dramatically reduced immunogenicity and antigenicity. Also, the polyalkylene oxide conjugates, when injected into a living organism, have been shown to remain in the bloodstream considerably longer than the corresponding native proteins. Examples of such therapeutic protein conjugates include tissue plasminogen activator, insulin, interleukin II and hemoglobin. In addition, PAO's have also been conjugated to oligonucleotides. See, for example U.S. Pat. No. 4,904,582.

To conjugate polyalkylene oxides, the hydroxyl endgroups of the polymer must first be converted into reactive functional groups. This process is frequently referred to as "activation" and the product is called an "activated polyalkylene oxide."

Until recently, covalent attachment of the polyalkylene oxide to an appropriate nucleophile was effected by activated polyalkylene oxides such as polyalkylene oxide succinoyl-N-hydroxysuccinimide ester, as disclosed by Abuchowski et al., *Cancer Biochem. Biophys.*, 7, 175–86 (1984). This polyalkylene oxide derivative is desirable because it is reactive under mild conditions.

A shortcoming associated with this derivative, however, is the fact that it is relatively hydrolytically unstable when no nucleophile is present. Recently, in U.S. Pat. No. 5,122,614, polyalkylene oxide-N-succinimide carbonates were disclosed having improved hydrolytic stability over the polyalkylene oxide succinoyl succinates. Even so, the pH conditions necessary to deprotonate the $\epsilon$—NH$_2$ groups of polypeptide lysines for conjugation subject the activated polyalkylene oxide to hydrolysis. This does not affect the reaction end product, other than to reduce its yield. While reduced yields ordinarily affect product cost, the hydrolysis becomes even more costly for several reasons. Firstly, reaction mixtures cannot be prepared significantly in advance. Additional purification of the end product is required to remove the hydrolytic degradation products. Furthermore, the reduction in yield is compensated for by increasing the amount of activated polyalkylene oxide starting material. This increases the viscosity of the reaction mixture, thereby further increasing the processing cost, and potentially interferes with downstream purification of the polymer and conjugate.

A need exists, therefore, for polyalkylene oxides that are unreactive towards weak nucleophiles such as water but react readily with stronger nucleophiles such as polypeptides. While thiazolidine thiones have been reported to react readily with lower alkyl and aryl primary and secondary amines to form desirable secondary and tertiary N-acyl (i.e., amide) derivatives, thiazolidine thione activated PAO's are unreported. (See, Fujita, *Pure Appl. Chem.*, 53(6), 1141–54 (1981)). The thiazolidine thione functions as a leaving group. The acyl thiazolidine thiones disclosed have a structure represented by Formula I:

in which R$_1$ is an alkyl, cycloalkyl, aryl, arylalkyl, alkoxy or phenyl moiety.

SUMMARY OF THE INVENTION

It has now been discovered that cyclic imide thione substituted polyalkylene oxides possess a desirable combination of nucleophilic reactivity and hydrolytic stability. For the conjugation of polyalkylene oxides with bioactive materials, the desired aminolysis predominates over hydrolysis, so that reactions in aqueous solutions occur with higher yields. The cyclic imide thione activated polyalkylene oxides have improved resistance to hydroxyl attack under the pH conditions which are required in order to deprotonate the protein amines.

Therefore, in accordance with the present invention there is provided a water-soluble cyclic imide thione activated polyalkylene oxide. Preferred cyclic imide thione activated polyalkylene oxides are represented by the structure of Formula II:

$$X—R—L—CO—R_3 \qquad (II)$$

wherein R is a water-soluble polyalkylene oxide;

R$_3$ is a cyclic imide thione, the imido nitrogen of which is covalently bonded to the carbonyl carbon;

X is a terminal moiety of the polyalkylene oxide; and

L is a hydrolytically stable moiety covalently linking the polyalkylene oxide and the carbonyl carbon. In one preferred aspect, L contains an oxygen on one end that forms a —O—CO—N linkage with the cyclic imide thione. R$_3$ is preferably one of the cyclic imide thiones depicted below:

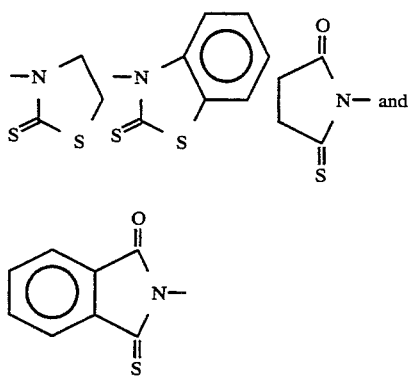

The depicted cyclic imide thiones illustrate that R$_3$ includes benzo imide thiones. Thiazolidine thiones are the more preferred cyclic imide thiones, with the thiazolidine thione depicted below being most preferred:

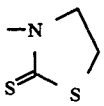

In accordance with the present invention, there is also provided a process for the preparation of water-soluble cyclic imide thione activated polyalkylene oxides, which process includes the steps of:

reacting a cyclic imide thione with a polyalkylene oxide having a structure corresponding to Formula III:

$$X-R-L-CO-Y \qquad (III)$$

so that an activated polyalkylene oxide is formed having a structure corresponding to Formula II, wherein R is a water-soluble polyalkylene oxide; X is a terminal moiety of the polyalkylene oxide; L is a moiety forming a hydrolytically stable, covalently bonded linkage between the polyalkylene oxide and the carbonyl carbon; and Y is a halogen; and recovering the cyclic imide thione activated polyalkylene oxide.

The cyclic imide thione activated polyalkylene oxides of the present invention react with biologically active nucleophiles to form covalently bonded conjugates thereof. When the biologically active nucleophile is a protein or polypeptide, conjugation occurs at the $\epsilon-NH_2$ moieties of lysines.

The present invention therefore also provides a method of forming a biologically active conjugate of a biologically active nucleophile and one or more water-soluble polyalkylene oxides covalently bonded thereto, which method includes the steps of:

contacting a biologically active nucleophile with a cyclic imide thione activated polyalkylene oxide, so that a biologically active conjugate of the biologically active nucleophile and the polyalkylene oxide is formed; and recovering the biologically active conjugate.

The hydrolytic stability of the cyclic imide thione activated polyalkylene oxides of the present invention permit bulk solutions of activated polyalkylene oxide to be prepared in advance of production runs. Furthermore, the cyclic imide thione group can be reacted with a variety of biologically active nucleophiles of interest other than lysine $\epsilon$-amino groups of polypeptides. For example, the activated polyalkylene oxides of the present invention will react with any primary or secondary amino group. The cyclic imide thiones will also react with other nucleophilic peptide groups, such as $\alpha$-amino groups, guanidino moieties, mercapto groups, and the like, at the appropriate pH. In addition, the heterobicyclic imide thiones are also reactive with nucleotides such as guanine, adenine, and the like, and derivatives thereof which possess nucleophilic amino groups.

The balance of hydrolytic stability and nucleophilic reactivity can be readily adjusted by variation of the hydrolytically stable group, L. For example, polyalkylene oxide succinimidyl carbonates typically have a half-life ($t_{\frac{1}{2}}$) of two hours at 7.0 pH and 27° C. Under the same conditions, when L is —O— and $R_3$ is a thiazolidine thione, the activated polyalkylene oxides of Formula II have a $t_{\frac{1}{2}}$ of greater than 120 hours, while when L is —OCH$_2$—, the same activated polyalkylene oxides have a $t_{\frac{1}{2}}$ of approximately ten hours. With respect to the reactivity of the activated polyalkylene oxides under the same conditions, the more stable activated polyalkylene oxides typically require longer reaction times to form conjugates with the $\epsilon$-amino groups of lysines of polypeptides such as hemoglobin, when all other conditions are maintained the same. Thus, the range of reactivity and the hydrolytic stability of the cyclic imide thiones of the present invention can be selected to meet the needs of particular end use applications.

DETAILED DESCRIPTION OF THE PREFERRED EMBODIMENT

The cyclic imide thione activated polyalkylene oxides of the present invention are preferably prepared from polyalkylene oxides that are soluble in water at room temperature. Polyalkylene oxides meeting this requirement are polyethylene glycol (PEG) and copolymers thereof. Block copolymers of PEG with polypropylene glycol or polypropylene oxide are also suitable for use with the present invention, provided that the degree of block copolymerization is not so great as to render the polymer insoluble in water at room temperature. Other polymers suitable for use with the present invention include polyacrylates, polymethacrylates and polyvinyl alcohols.

The molecular weight of the polyalkylene oxide will depend mainly upon the end use of a particular polymer conjugate. Those of ordinary skill in the art are capable of determining molecular weight ranges suitable for their end-use applications. In general, the useful range of molecular weight is a number average molecular weight between about 600 and about 100,000 daltons, and preferably between about 2,000 and about 20,000 daltons. A molecular weight of 5,000 daltons is most preferred.

Preferred cyclic imide thione activated polyalkylene oxides are represented by the structures of Formula II wherein R is a water-soluble polyalkylene oxide, L is a moiety forming a hydrolytically stable, covalently bonded linkage between the polyalkylene oxide and the carbonyl carbon, $R_3$ is a cyclic imide thione, the imido nitrogen of which is covalently bonded to the carbonyl carbon, and X is a terminal moiety of the polyalkylene oxide.

X can be a group into which a terminal hydroxyl group may be converted, including the reactive derivatives of the prior art disclosed in U.S. Pat. Nos. 4,179,337, 4,847,325, 5,122,614 and in copending and commonly owned U.S. patent application Ser. No. 626,696, filed Mar. 18, 1991, now U.S. Pat. No. 5,173,354 the disclosures of all of which are hereby incorporated herein by reference thereto. The heterobifunctional polymers can be prepared by methods known to those skilled in the art without undue experimentation.

X can also be a cyclic imide thione derivative having the structure of Formula IV:

$$-L-CO-R_3 \qquad (IV)$$

wherein L and $R_3$ are the same as disclosed above with respect to Formula II. When the moieties selected for L on both ends of the polymer are identical, the polymer will then be a symmetrical, homobifunctional polymer derivative.

Such double polymer substitution can result in either intra- or intermolecular crosslinking of the nucleophile, which, in some cases, can be useful. Such crosslinking can be controlled by the amount of polymer used and the concentration of reacting species, which methods are well-known to those of ordinary skill in the art.

Crosslinking can also be prevented by using a preblocked polymer having only one labile hydroxyl group per polymer moiety. In such polymers, X would represent a blocking group such as an alkoxy group of one to four carbon atoms. The preferred blocking group is a methoxy group. For the preparation of homobifunctional and monofunctional polymer derivatives, see Buckmann et al., *Makromol. Chem.*, 182(5, 1379–84 (1981). X can also represent an antibody or solid support covalently coupled to the polymer by methods known to those skilled in the art as illustrated in EP 295,073.

The cyclic imide thiones are preferably 2-thiones. The cyclic imide thiones preferred for $R_3$ are depicted below and include benzo imide thiones:

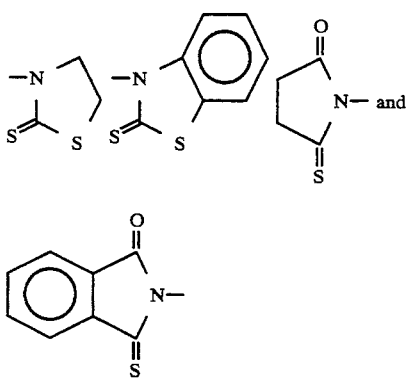

Thiazolidine thiones are the more preferred cyclic imide thione, with the thiazolidine thione depicted below being most preferred:

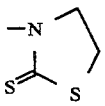

The benzene ring of benzo imide thiones may be substituted or unsubstituted.

The cyclic imide thione activated polyalkylene oxides of Formula II are formed by reacting a cyclic imide thione with a polyalkylene oxide having a structure represented by Formula III, wherein X, R and L are the same as described above with respect to Formula II and Y is a halogen. A common non-hydroxyl solvent such as toluene and a reaction temperature between about 25° C. and about 40° C. is employed. All materials must be essentially free of water. Scrupulous care must be taken not to contaminate the reaction mixture with water to avoid hydrolysis of the acid halide or chloroformate.

When the halogen Y is Cl, the polyalkylene oxide is an acid chloride or chloroformate derivative, which is formed from polyalkylene oxide carboxylic acids, or alcohols, by well known and conventional methods. Polyalkylene oxide acid chlorides can be prepared by the method disclosed by Buckmann et al. *Makromol. Chem.*, 182(5), 1379–84 (1981), or by the method of U.S. Pat. No. 5,122,614.

The moieties represented by L that are capable of forming a hydrolytically stable, covalently bonded linkage between a polyalkylene oxide and the carbonyl carbon are well-known to those of ordinary skill in the art. A wide variety of linking groups may be employed, a number of which are prepared from commercially available activated polyalkylene oxides extensively used for linking macromolecules. The linking groups include, for example, —O—, —NH—, —NH—CO(CH$_2$-)$_z$—, —NH—CO(CH$_2$)$_z$O—, —S—, —CO—NH(CH$_2$-)$_z$—, —CO—NH(CH$_2$)$_z$O—, —O(CH$_2$)$_z$O—, —SCH$_2$CH$_2$—, —O(CH$_2$)$_z$— and —NH(CH$_2$)$_z$—, wherein z is an integer from one to ten and preferably from one to six, inclusive.

In one aspect of the invention, L preferably contains an oxygen on one end that forms a —O—CO—N linkage with the cyclic imide thione. The resulting cyclic imide thione will react with amines to form linkages containing urethane moieties. The preferred L which forms a urethane moiety is —O—.

In another aspect of the invention, L can contain an amine on one end that forms a —NH—CO—N linkage with the cyclic imide thione. The resulting cyclic imide thione will react with amines to form linkages containing urea moieties. The preferred L which forms a urea moiety is —NH—. The polyalkylene oxide derivative of Formula III in which L is —O— and Y is a halogen such as Cl can be obtained by reacting a polyalkylene oxide with phosgene as described in the above-cited U.S. Pat. No. 5,122,614. The polyalkylene oxide derivative of Formula III in which L is —NH— and the halogen Y is Cl can be obtained by reacting a polyalkylene oxide amine with phosgene under the same conditions described in U.S. Pat. No. 5,122,614.

L also preferably contains an alkyl group on one end, such as —OCH$_2$—, that forms a —OCH$_2$—CO—N linkage with the cyclic imide thione. The resulting cyclic imide thione will react with amine groups to form linkages containing amide moieties. The preferred L which forms an amide moiety is —OCH$_2$—. The polyalkylene oxide derivative of Formula III in which L is —OCH$_2$— and the halogen Y is Cl is a polyalkylene oxide carboxylic acid chloride, the preparation of which is discussed above.

A polyalkylene oxide derivative of Formula III in which L is —CO—NH—(CH$_2$—)$_z$—O— and the halogen Y is Cl can be obtained by reacting a polyalkylene oxide carboxylic acid with an hydroxy alkyl amine by either first forming the acid chloride or by utilizing a carbodiimide mediated reaction. The resulting compound is then reacted with phosgene. The derivative in which L is —NH—CO(CH$_2$—)$_z$—O— and the halogen Y is Cl is obtained by reacting a polyalkylene oxide amine with a hydroxy carboxylic acid by either first forming the acid chloride or by utilizing a carbodiimide mediated reaction, and then reacting the resulting compound with phosgene. Either acid chloride can be converted to the carboxylic acid by conventional methods.

The stoichiometry and reaction conditions for the foregoing reactions are well understood and essentially conventional. The reactions are also carried out in non-hydroxyl solvents in which the reactants are soluble, such as toluene. Reaction temperatures between 20° C. and 50° C. are suitable, and temperatures between 35° C. and 40° C. are preferred. Again, all materials must be essentially water-free. The adaption of the above reactions to obtain a bifunctional polyalkylene oxide is also well understood by one of ordinary skill in the art. (See, Buckmann et al., *Makromol. Chem.*)

The cyclic imide thione activated polyalkylene oxides are purified from low molecular weight materials by conventional methods. The cyclic imide thiones can then be reacted with biologically active nucleophiles to form a linkage between the polyalkylene oxide and the biologically active nucleophile. The resulting product represents a biologically active conjugate of the nucleophile and the polyalkylene oxide.

The term "hydrolytically stable" means that the cyclic imide thione activated polyalkylene oxides of the present invention, in aqueous solution, will not undergo substantial degradation at physiological pH and at temperatures up to 27° C. Degradation of less than 50% under these conditions over an eight hour time period is considered insubstantial. At 4° C., substantially less degradation is expected.

The term "biologically active" is used with respect to the nucleophiles of the present invention consistently with the meaning commonly understood to those of ordinary skill in the art, which meaning is not limited to physiological or pharmacological activities of the nucleophiles in the therapeutic sense. For example, many physiologically active nucleotides such as enzymes, the polyalkylene oxide conjugates of which may not have therapeutic applications, are able to catalyze reactions in organic solvents. Likewise, regardless of the therapeutic uses for polyalkylene oxide conjugates of proteins such as concanavalin A, immunoglobulins, and the like, the polyalkylene oxide conjugates of these proteins are also useful as laboratory diagnostic tools.

Therefore, the biologically active nucleophiles of interest to the present invention include a variety of enzymes, including, but not limited to, carbohydrate-specific enzymes, proteolytic enzymes, and the like. Enzymes of interest, for both biological applications in general and therapeutic applications in particular include the oxidoreductases, transferases, hydrolases, lyases, isomerases and ligases disclosed by U.S. Pat. No. 4,179,337, the disclosure of which is hereby incorporated herein by reference thereto. Without being limited to particular enzymes, examples of specific enzymes of interest include asparaginase, arginase, adenosine deaminase, superoxide dismutase, catalase, chymotrypsin, lipase, uricase and bilirubin oxidase. Carbohydrate-specific enzymes of interest include glucose oxidase, glucosidase, galactosidase, glucocerebrosidase, glucuronidase, etc.

The biologically active nucleophiles of the present invention also include proteins of general biological or therapeutic interest, including, but not limited to, hemoglobin and serum proteins such as Factor VIII, Factor IX, immunoglobulins, lectins, interleukins, interferons and colony stimulating factors, and ovalbumin and bovine serum albumin (BSA). Other proteins of general biological or therapeutic interest include hormones such as insulin, ACTH, glucagon, somatostatin, somatotropins, thymosin, parathyroid hormone, pigmentary hormones, somatomedins, erythropoietin, luteinizing hormone, hypothamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Certain of the above proteins such as the interleukins, interferons and colony stimulating factors also exist in non-glycosilated form, usually the result of preparation by recombinant protein techniques. The non-glycosilated versions are also among the biologically active nucleophiles of the present invention.

Other proteins of interest are allergen proteins disclosed by Dreborg et al., *Crit. Rev. Therap. Drug Carrier Syst.*, 6, 315–65 (1990) as having reduced allergenicity when conjugated with polyalkylene oxides, and consequently suitable for use as tolerance inducers. Among the allergins disclosed are ragweed Antigen E, honeybee venom, mite allergen, and the like.

Other biologically active nucleophiles of the present invention include antibodies, antibody fragments, single chain antigens, nucleotides and oligonucleotides. The coupling of oligonucleotides to polyalkylene oxides is disclosed by the above-cited U.S. Pat. No. 4,904,582. Still other biologically active nucleophiles included within the scope of the present invention are therapeutically active nucleophilic compounds. Of the therapeutically active nucleophilic compounds, chemotherapeutic molecules having appropriately reactive nucleophilic moieties are particularly preferred. For example, anti-tumor agents, anti-infective agents, and the like, or, in general, pharmaceutical chemicals containing an appropriate nucleophilic group, are included within the scope of the present invention.

One or more polyalkylene oxides can be attached covalently to the biologically active nucleophile by reacting the polyalkylene oxide cyclic imide thione with the nucleophile. The cyclic imide thione functions as a leaving group to form a linkage covalently bonding the nucleophile to the polyalkylene oxide. When the nucleophile is a protein or polypeptide, conjugation occurs at the $\epsilon$—$NH_2$ moieties of lysines to form hydrolytically stable linkages. Amide and urethane linkages are preferred.

For nucleophiles such as polypeptides, more than one polyalkylene oxide conjugate per nucleophile is preferred. The degree of conjugation is limited only by the number of $\epsilon$—$NH_2$ moieties of lysines. The optimum degree of conjugation can be readily determined for a particular nucleophile by one of ordinary skill in the art without undue experimentation. The degree of conjugation may be modified by varying the reaction stoichiometry using well-known techniques. Typically, more than one polyalkylene oxide conjugate per nucleophile is obtained by utilizing a stoichiometric excess of the activated polyalkylene oxide.

The reaction of the cyclic imide thione activated polyalkylene oxides of Formula II with the $\epsilon$—$NH_2$ moieties of polypeptide lysines to form an amide linkage is illustrated by the reaction sequence depicted below in which R and X are the same as described above with respect to Formula II, L is —$OCH_2$—, $R_2$ represents the balance of the polypeptide, and $R_3$ of Formula II is a thiazolidine thione:

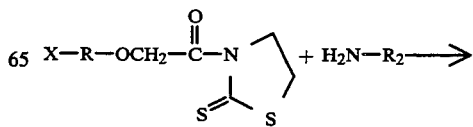

-continued

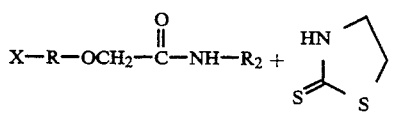

Urethane linkages are obtained by substituting an —O—CO— group for the —OCH$_2$—CO— group of the activated polyalkylene oxide.

The biologically active nucleophiles may be reacted directly with the cyclic imide thione activated polyalkylene oxides in an aqueous reaction medium. This reaction medium may also be buffered, depending upon the pH requirements of the nucleophile. The optimum pH for the reaction is generally between about 6.5 and about 8.0 and preferably about 7.4.

In all instances, the optimum reaction medium pH for the stability of particular nucleophiles and for reaction efficiency, and the buffer in which this can be achieved, is readily determined within the above ranges by those of ordinary skill in the art without undue experimentation. For purposes of this application, the operativeness of the within reactions under mild conditions is defined as meaning that the preferred temperature range is between about 4° and about 37° C.

Those of ordinary skill in the art will understand that the reactions will run somewhat faster to completion at higher temperatures, with the proviso that the temperature of the reaction medium cannot exceed the temperature at which the nucleophile may denature or decompose. Furthermore, those of ordinary skill in the art will understand that certain nucleophiles, particularly polypeptides, will require reaction with the cyclic imide thione activated polyalkylene oxides at reduced temperatures to minimize loss of activity and/or to prevent denaturing. The reduced temperature required by particular polypeptides is preferably no lower than 4° C. and in no event should this temperature be lower than 0° C. The reaction will still take place, although longer reaction times may be necessary.

Usually, the nucleophile is reacted in aqueous solution with a quantity of the cyclic imide thione activated polyalkylene oxide in excess of the desired degree of conjugation. Following the reaction, the conjugated product is recovered and purified by diafiltration, column chromatography or the like.

In view of the foregoing, it can be readily appreciated that the cyclic imide thione activated polyalkylene oxides of the present invention possess the optimum balance of reactivity and hydrolytic stability so that polymer conjugates can be formed with biologically active nucleophiles with an insubstantial amount of hydrolytic degradation of the activated polyalkylene oxide. Thus, reaction yields are increased and process costs are reduced.

The following non-limiting examples illustrate certain aspects of the invention. All parts and percentages are by weight unless otherwise noted, and all temperatures are in degrees Celsius.

EXPERIMENTAL

Example 1

A thiazolidine thione activated PEG of Formula II, in which L is —OCH$_2$—, was prepared by first adding to 75 mL toluene, 5.0 g (1 mmol.) of m-PEG carboxylic acid. The m-PEG carboxylic acid was synthesized according to Veronese, *J. Controlled Release*, 10(1), 145–54 (1989) and had a number average molecular weight of 5,000 daltons. The resulting mixture was refluxed for two hours, under nitrogen, in a flask equipped with a Dean-Stark trap. During this time, a total of 25 mL of the solvent was removed from the trap.

The reaction mixture was then cooled to 30° C., followed by addition of 0.3 g (2 mmol.) of oxalyl chloride (Aldrich Chemical) and one drop of dimethyl formamide. This mixture was then stirred overnight at 40° C. followed by the addition of 0.4 g (3 mmol.) of 2-mercaptothiazoline (Aldrich Chemical) and 0.3 mL (3 mmol.) of triethyl amine. The reaction mixture was stirred an additional six hours, followed by filtration, and removal of the solvent by distillation in vacuo. The crude residue was recrystallized from 100 mL of 2-propanol to yield 4.3 g product. The $^{13}$C NMR spectrum was consistent with a thiazolidine thione activated PEG in which L is —OCH$_2$—: C=S, 200.5 ppm; C=O, 170.9 ppm; CH$_2$—N, 54.8 ppm; CH$_2$—S, 28.5 ppm; OCH$_3$, 58.0 ppm.

Example 2

A thiazolidine thione activated PEG of Formula II in which L is —O— was prepared by adding 100 g (20 mmol.) m-PEG—OH (Union Carbide) to one liter of toluene. The m-PEG—OH had a number average molecular weight of 5,000 daltons. The solution was refluxed for four hours, under nitrogen, in a flask equipped with a Dean-Stark trap. During this time, a total of 200 mL of solvent was removed from the trap. The reaction mixture was then cooled to 40° C., followed by the addition of 2.4 g (8 mmol.) of triphosgene (Aldrich Chemical) and 3.1 mL (20 mmol.) of triethylamine. This mixture was stirred for four hours at 40° C., followed by the addition of 3.0 g (25 mmol.) of 2-mercaptothiazoline and 3.5 mL (25 mmol.) of triethylamine. The resulting mixture was then stirred overnight at 40° C., followed by filtration through CELITE ®, and removal of the solvent from the filtrate by distillation in vacuo. The crude residue was recrystallized from two liters of 2-propanol to yield 90.3 g of product. The $^{13}$C NMR spectrum was consistent with a thiazolidine thione activated PEG of Formula II in which L is —O—: C=S, 198.7 ppm; C=O, 149.8 ppm; CH$_2$—N, 54.8 ppm; CH$_2$—S, 27.2 ppm; OCH$_3$, 57.8 ppm.

Example 3

The thiazolidine thione activated PEG of Example 1 was conjugated with bovine hemoglobin by first preparing a 10 mL solution of pH 7.8 phosphate buffer by dissolving 0.1380 g NaH$_2$PO$_4$.H$_2$O, 0.2681 g Na$_2$HPO$_4$.7H$_2$O and 0.2338 g NaCl in 7.0 mL deionized water. The pH of this solution was then adjusted to 7.8 with 1.0N NaOH and diluted to 10 mL with deionized water. A 4.0 mL sample of isolated bovine hemoglobin (10.9%, 7.02×10$^{-6}$ mol.) was measured into a 50 mL jacketed beaker chilled to 4° C. by means of a refrigerated recirculating bath. A thermometer and pH electrode were placed in the hemoglobin solution, which was stirred magnetically. The pH of the hemoglobin was adjusted to 7.8 with 1.0N NaOH or 1.0N HCl as necessary.

To this was added 0.6483 g of the thiazolidine thione activated PEG (1.26×10$^{-4}$ mmol.) followed by 4.0 mL of the pH 7.8 phosphate buffer prepared above. The mixture was allowed to stir at 4° C. for one hour while maintaining pH 7.8 with dropwise additions of 1.0N NaOH or 1.0N HCl. After one hour of reaction time, 0.0420 g (2.39×10⁻⁴ mol.) of cysteine HCl was added, followed by 0.0095 g (1.26×10⁻⁴ mol.) of glycine. The pH was adjusted up to 7.8 using 1.0N NaOH, and the mixture was allowed to stir for 15 minutes. The product was stored in a 4° C. refrigerator. The final hemoglobin concentration of the product was 4.5%. Capillary zone electrophoresis results indicate that PEG conjugation of the hemoglobin was effected by this procedure.

As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A water-soluble cyclic imide thione activated polyalkylene oxide, comprising a structure represented by:

X—R—L—CO—R₃ wherein:

R is a polyalkylene oxide residue having a number average molecular weight between 600 and 100,000 daltons;

R₃ is selected from the group consisting of:

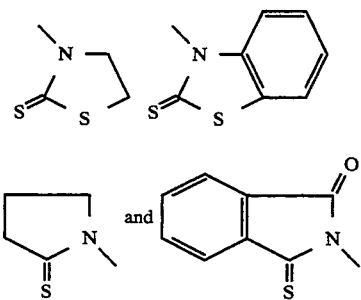

L is a moiety forming a covalent linkage between R and the carbonyl carbon, said moiety being hydrolytically stable at physiologic pH and temperatures up to 27° C.; and X is a terminal moiety of said polyalkylene oxide selected from the group consisting of alkoxy moieties containing up to four carbon atoms and —L—CO—R₃.

2. The activated polyalkylene oxide of claim 1, wherein said polyalkylene oxide is selected from the group consisting of polyethylene glycol and block copolymers of polyethylene glycol and polypropylene glycol.

3. The activated polyalkylene oxide of claim 2, wherein said polyalkylene oxide is polyethylene glycol.

4. The activated polyalkylene oxide of claim 1, wherein said polyalkylene oxide has a number average molecular weight between about 2,000 and about 20,000 daltons.

5. The activated polyalkylene oxide of claim 4, wherein said polyalkylene oxide has a 5,000 dalton number average molecular weight.

6. The activated polyalkylene oxide of claim 1, wherein X is a methoxy moiety.

7. The activated polyalkylene oxide of claim 1, wherein L is a moiety selected from the group consisting of —O—, —NH—, —OCH₂—, —NH—CO(CH₂)$_z$—, —NH—CO(CH₂)$_z$O—, —CO—NH(CH₂)$_z$—, —S—, —CO—NH(CH₂)$_z$O—, —O(CH₂)$_z$O—, —O(CH₂)$_z$—, —SCH₂CH₂— and —NH(CH₂)$_z$— moieties, wherein z is an integer between one and ten, inclusive.

8. The activated polyalkylene oxide of claim 1, wherein R₃ is a benzo imide thione.

9. The activated polyalkylene oxide of claim 1, wherein R₃ is:

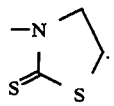

10. The activated polyalkylene oxide of claim 1, wherein R₃ is

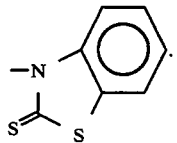

* * * * *